United States Patent [19]

Crawford et al.

[11] Patent Number: 4,726,826
[45] Date of Patent: Feb. 23, 1988

[54] METHOD FOR PARTIAL CONDENSATION OF HYDROCARBON GAS MIXTURES

[75] Inventors: Duffer B. Crawford; T. Michael O'Connor; Ramanathan R. Tarakad, all of Houston, Tex.

[73] Assignee: The M. W. Kellogg Company, Houston, Tex.

[21] Appl. No.: 74,732

[22] Filed: Jul. 17, 1987

[51] Int. Cl.$^4$ .................................................. F25J 3/00
[52] U.S. Cl. ........................................... 62/20; 62/27; 62/29; 62/42
[58] Field of Search ............. 62/9, 11, 16, 17, 20, 62/23, 24, 27, 29, 31, 32, 34, 36, 42; 55/68, 69

[56] References Cited

U.S. PATENT DOCUMENTS

| | | | |
|---|---|---|---|
| 2,833,127 | 5/1958 | Vesque et al. | 62/27 X |
| 2,964,915 | 12/1960 | Hull | 62/24 |
| 3,100,147 | 8/1963 | Hull | 62/37 |
| 3,370,435 | 2/1968 | Arreger | 62/29 X |
| 3,392,536 | 7/1968 | Smith | 62/29 X |
| 3,818,718 | 6/1974 | Freese | 62/272 |
| 3,919,853 | 11/1975 | Rojey | 62/9 |
| 4,330,307 | 5/1982 | Coury | 62/23 |
| 4,410,342 | 10/1983 | Horton | 62/23 |
| 4,444,016 | 4/1984 | Banerjee | 62/11 X |
| 4,502,877 | 3/1985 | Bacon, Sr. | 62/42 |
| 4,609,390 | 9/1986 | Wilson | 62/21 |
| 4,639,262 | 1/1987 | Heichberger | 62/11 |

*Primary Examiner*—Steven E. Warner

[57] ABSTRACT

Heavy components of hydrocarbon gas mixtures are recovered through partial condensation of a first portion of the starting gas by indirect heat exchange with a refrigerant wherein the condensate formed is entrained in the gas stream. The condensate is separated from the resulting partially condensed, two-phase mixture and the separated condensate is then thermally stripped of light components by heat exchange with a second portion of the starting gas which is thereby also partially condensed. Heavy components from the starting gas mixture are recovered as stripped hydrocarbon condensate.

12 Claims, 4 Drawing Figures

METHOD FOR PARTIAL CONDENSATION OF HYDROCARBON GAS MIXTURES

This invention relates to dephlegmation of gas mixture containing condensable components. More particularly, this invention relates to partial condensation of hydrocarbon gas mixture in which the starting gas is cooled by heat exchange in one or more stages to condense and separate less volatile components from the gas mixture.

Hydrocarbon gas mixture such as natural gas and refinery gas are typically treated for removal of $C_3+$ components for further processing, for example, into a liquefied petroleum gas (LPG) stream. The starting gas mixture relevant to the present invention may contain components within the range of $C_1$ to $C_6$ hydrocarbons optionally associated with nitorgen in the case of natural gas or hydrogen in the case of refinery gas.

Partial condensation is a well established method of separating easily condensed components from these gas streams when precise separations are not desired, for example, in condensate recovery from field gas and in initial separation stages of cryogenic plants for production of LPG.

Typically, dephlegmation has been carried out by partial condensation in vertical tubular heat exchangers in which the starting gas mixture flows upwardly and is partially condensed in the warm tube side of the exchanger by a refrigerant employed in the cold shell side. Gas velocities in the warm side are very low, below the entrainment velocity, so that the heavy components condensed on the tube wall interiors flow downwardly countercurrent to the upward flow of gas being treated. In simple configurations of the method, the condensate is recovered from the bottom of the exchanger and light gas, which is more volatile than the starting gas, is recovered from the top of the exchanger. One particular example of a low velocity partial condensation system is described in U.S. Pat. No. 3,100,147.

Practitioners have appreciated that low velocity partial condensation is inherently poor in heat transfer efficiency and such systems are, therefore, quite costly. More recently, high velocity partial condensation has been used in which a two phase gas mixture is produced and directed to an external gas/liquid separator for recovery of condensate. One of the principle problems with this condensation method is that, because of cocurrent gas/liquid flow at or above liquid entrainment velocity in the condenser, the recovered condensate retains some light gas which must be removed in a separate stripping step. In result, the improvement in heat exchange due to high velocity partial condensation is, to significant extent, offset by increased complexity, cost, and plot space requirements of the high velocity methods.

It is, therefore, an object of this invention to achieve the improved heat transfer characteristics of high velocity partial condensation while retaining the better separation characteristics of low velocity partial condensation.

According to the invention, a first portion of a starting gas mixture is partially condensed to a two phase mixture in indirect heat exchange with a refrigerant and condensate is separated from the two phase mixture. A second, parallel portion of the starting mixture is separately partially condensed by heat exchange with condensate recovered from the first portion while the recovered condensate is thermally stripped by heat from the second, parallel portion.

FIG. 1 illustrates an embodiment of the invention wherein the first partial condensation zone is a vertical tubular heat exchanger, the second partial condensation zone is a bubble cap column, and the two phase mixture leaving the first partial condensation zone is separated in an external drum separator where first and second light gases from the respective partial condensation zones are combined.

Figure 4:
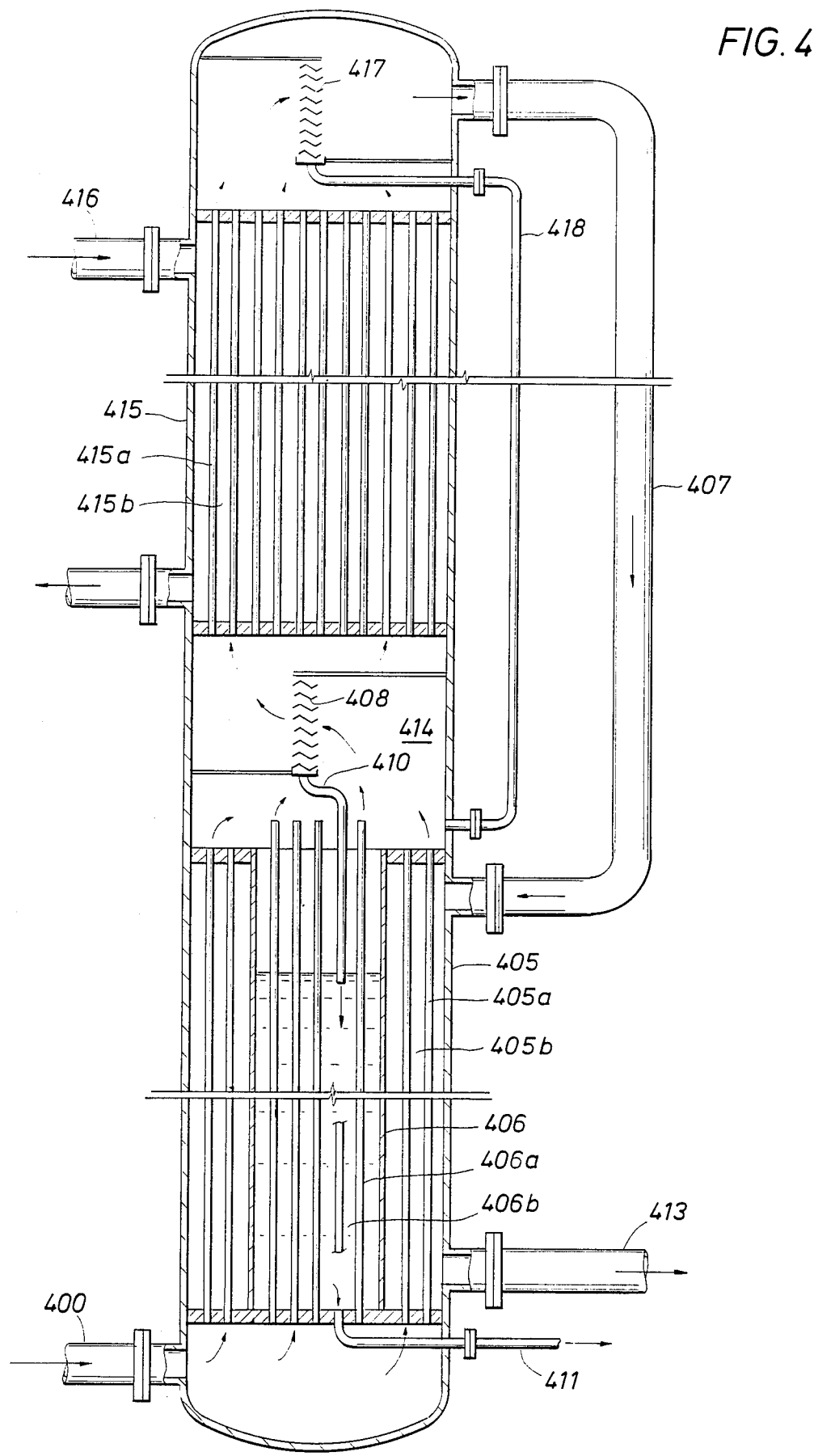

FIG. 4 illustrates a preferred multi-stage embodiment of the invention which employs a third partial condensation zone in series with the parallel first and second partial condensation zone. In this embodiment, a first gas/liquid separation zone is embodied by an impingement separator located between the series condensation stages. Likewise, a second gas/liquid separation zone is embodied by another internal impingement separator located above the upper tubular exchanger which is a suitable embodiment of the third partial condensation zone.

In one embodiment of the invention, therefore, the second portion of the starting gas mixture is partially condensed by direct heat exchange with condensate recovered from the first portion, that is to say, by direct heat exchange.

In another embodiment of the invention, the second portion is partially condensed by indirect heat exchange with the recovered first condensate.

In a preferred embodiment of the invention, light gases from the partially condensed first and second portions of the starting gas are combined and further partially condensed by indirect heat exchange in a third partial condensation zone. Most preferably, light gas recovered from partial condensation of the combined first and second light gases is employed as the first refrigerant in partial condensation of the first portion of the starting gas. When, in this embodiment, the starting gas mixture contains principally $C_1$ to $C_3$ hydrocarbons, mixed refrigerant containing $C_1$ up to $C_5$ hydrocarbons will preferably be employed as a second refrigerant in the third partial condensation zone at a temperature between $-45°$ C. and $-85°$ C.

Figure 1:
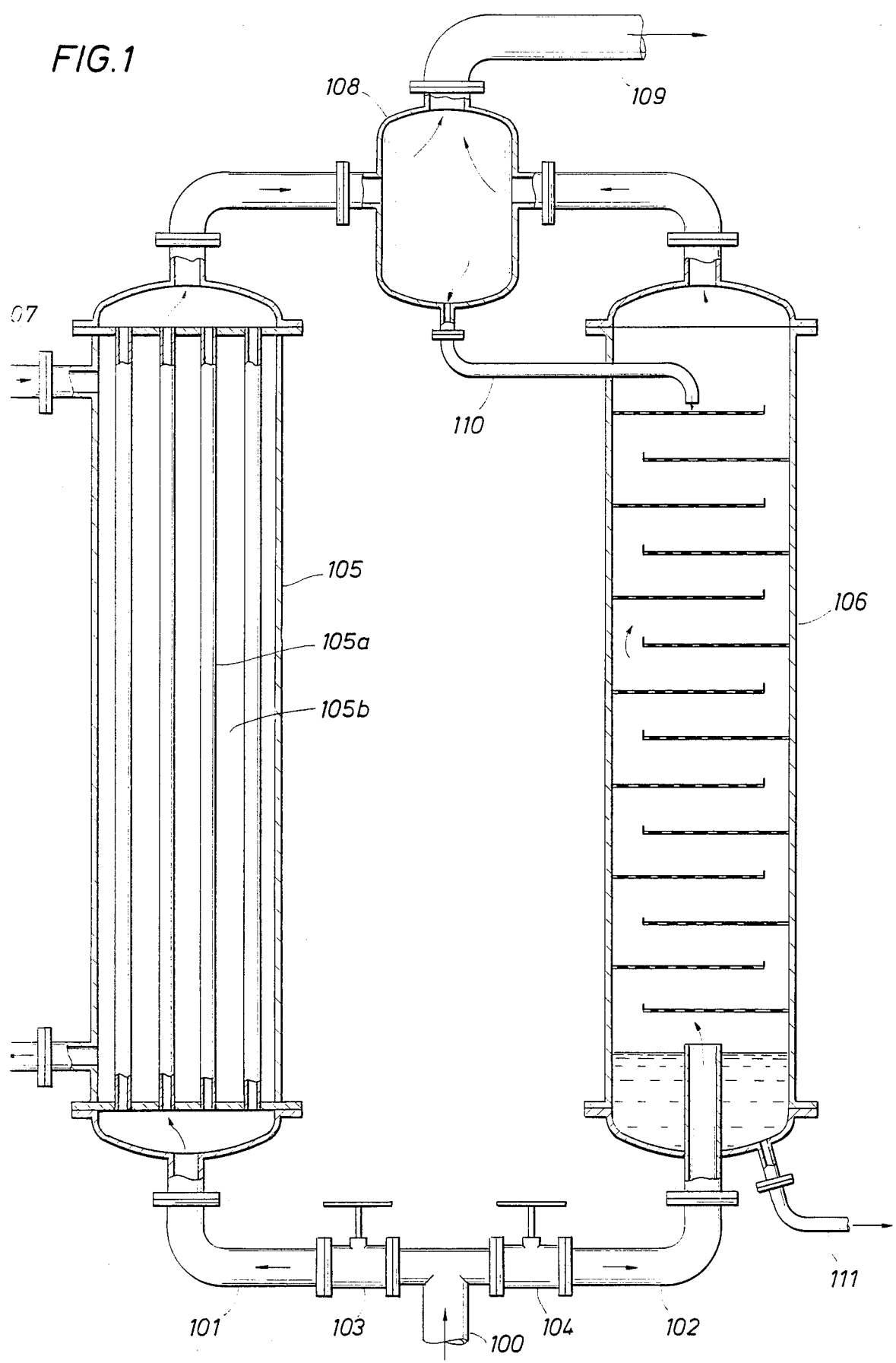

When processing gas mixtures containing components within the range of $C_1$ to $C_6$ hydrocarbons, the partial condensation method of the invention will usually be operated within a pressure range from 32 to 60 $kg/cm^2a$. The first, second, and, when used, third partial condensation zones as well as the gas/liquid separation zones operate at substantially the same pressure. That is to say that the first condensate recovered from the first partial condensation zone and employed as refrigerant in the second partial condensation zone is not expanded. Therefore, the stripped hydrocarbon condensate recovered from the second partial condensation zone is at substantially the same pressure as the gas mixtures introduced to the first and second partial condensation zones. Within this uniform pressure condition, when the second partial condensation zone is operated in a flooded condition on the cold side as will be later described, the stripped hydrocarbon condensate is recovered from the second partial condensation zone under a hydrostatic head with respect to the first and second portions of the starting gas between 3 and 14 meters. When the cold side of the second partial condensation zone is not operated under flooded conditions, for example, as illustrated in FIG. 1, the foregoing pressure conditions will be essentially the same.

Since the first refrigerant introduced to the cold side of the first partial condensation zone is necessarily colder than the recovered first condensate employed as refrigerant in the second partial condensation zone, more refrigeration is available in the first partial condensation zone than in the second. Accordingly, the first portion of the starting gas mixture will be between 70 and 95 mole percent of the starting mixture with, preferably, the balance going to the second partial condensation zone. Further parallel portions of the starting gas may be processed in further parallel partial condensation zones, but this will not usually be necessary or desirable.

As previously noted, the starting gas mixture is typically a field or refinery gas from which gas liquids are to be separated for sale or further processing and, therefore, the starting gas mixture is a single stream. It may be noted, however, that two independent process streams having substantially the same composition and at substantially the same operating conditions are equivalent to the divided portions of the starting gas mixture as described above. This particular circumstance of substantially identical process streams will not often occur.

Referring now to the drawings, it is noted that the first digit of the three digit reference numerals corresponds to the Figure number whereas the second and third digits identify functionally corresponding elements in all the drawings.

In FIG. 1, which illustrates the general method of the invention, the starting hydrocarbon gas mixture is introduced through line 100, divided into first and second parallel portions in, respectively, lines 101 and 102 by ratio control valves 103 and 104, and introduced respectively to first partial condensation zone 105 and second partial condensation zone 106. The first partial condensation zone (X)05 is always an indirect heat exchange zone illustrated here by an exchanger having a warm tube side 105a and a cold shell side 105b which contains a first refrigerant introduced through line 107.

The first portion of the starting gas flows upwardly through tubes 105a at a velocity above the entrainment mass velocity of condensate being formed, preferably between 25 and 500 kg/sec/m$^2$, such that a first condensate is entrained in a first light gas as a two phase mixture which is recovered from the first partial condensation zone and introduced to a first gas/liquid separation zone which is shown, not to scale, by drum separator 108. The drum separator provides disengagement space not usually available in a heat exchanger.

A second hydrocarbon gas mixture containing at least the first light gas is recovered from the separation zone through line 109 and condensate from at least the first portion of the starting gas is recovered from the first separation zone through line 110.

The second portion of the starting gas flows upwardly through the second partial condensation zone 106 which is illustrated in FIG. 1 as a bubble cap and tray gas/liquid contactor. The recovered first condensate in line 110 is introduced to the upper region of the second partial condensation zone and flows downwardly in direct contact heat exchange with the second portion of the starting gas. In this embodiment, the second condensate formed from the second gas portion combines with the downwardly flowing recovered first condensate and, accordingly, the recovered first condensate as well as the second condensate are thermally stripped by relatively long residence time contact with upwardly flowing warm gas. The resulting stripped hydrocarbon condensate accumulates in the lower region of the second partial condensation zone 106 and is recovered for sale or further processing through line 111. The remaining light gases separated in drum separator 108 are also recovered as a second hydrocarbon gas mixture through line 109 for sale or further processing.

It is essential that the first condensate be separated from the first light gas for use as refrigerant in the second partial condensation zone. It is not, however, essential that the second light gas recovered from the second partial condensation zone be introduced to the first gas/liquid separation zone or combined with the first light gas as illustrated in FIG. 1. Moreover, when the second partial condensation zone employs a direct contact condenser, the second condensate combines with the first condensate within the condenser and, in such instance, it is not necessary to introduce the second light gas to any separation zone.

Figure 2:
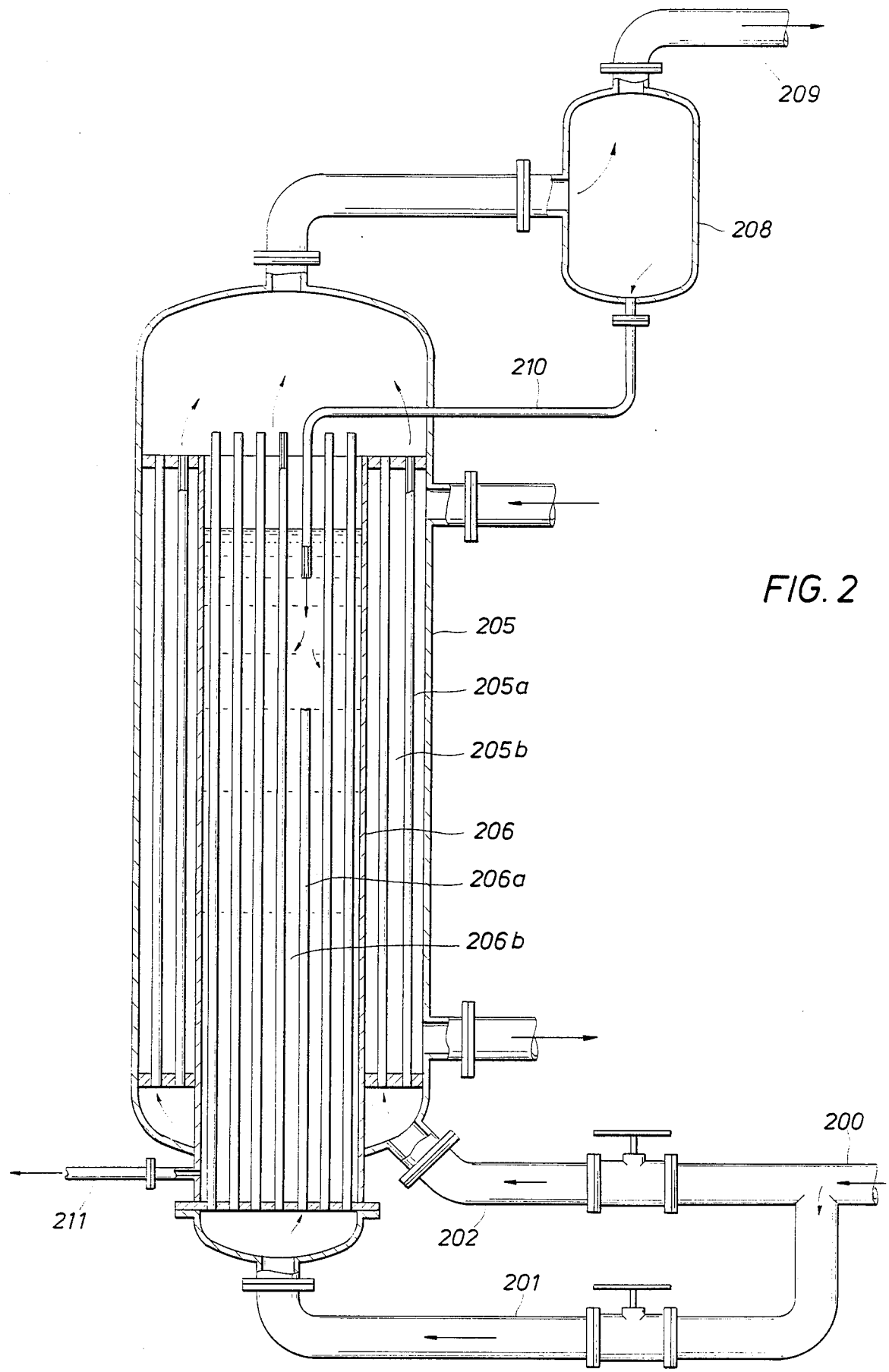
FIG. 2 illustrates another embodiment of the invention wherein the first partial condensation zone is an annular tubular heat exchanger and the second partial condensation zone is a vertical, tubular exchanger disposed centrally within the annular exchanger. In this embodiment, two phase mixtures are recovered from each of the partial condensation zones for subsequent external separation.

In FIG. 2, the starting hydrocarbon gas mixture introduced through line 200 is divided into first and second parallel portions in, respectively, lines 201 and 202 by ratio control valves and introduced respectively to first partial condensation zone 205 and second partial condensation zone 206. Again, the first partial condensation zone is an indirect heat exchange zone having a warm tube side 205a and a cold shell side 205b. Operation of the first partial condensation zone in FIG. 2 is similar to operation of the first partial condensation zone of FIG. 1 wherein a two phase mixture from this zone is introduced to a first separation zone indicated by separator drum 208 from which a second hydrocarbon gas mixture is recovered through line 209 and the first condensate is recovered through line 210.

As previously noted, the second partial condensation zone 206 is an indirect heat exchange zone having a warm tube side 206a and a cold shell side 206b that is contained within an annular tubular exchanger comprised by the first partial condensation zone. In this embodiment, both the first and second portions of the starting gas mixture pass through their respective parallel partial condensation zones at sufficiently high velocities to entrain the condensates formed and two phase mixtures are recovered from each of the condensation zones and then combined. In FIG. 2 the combined mixtures undergo phase separation in an external separtor, however, it may be preferred to use an internal impingement separator in the vapor space above the tubes as will be later described in connection with FIG. 4.

In FIG. 2, the recovered first and second condensates in line 210 are returned as refrigerant to the cold shell side 206b of the second partial condensation zone.

Here, the shell side of the second condensation zone is operated under flooded condition which provides the advantage of a hydrostatic head for easy recovery of the stripped hydrocarbon condensate, usually without need for a pump. It may be noted that the inner wall separating the first and second partial condensation zones fortunately has negligible heat transfer surface in comparison with the tube area of the exchanger so that the cold first refrigerant in the shell side of the first partial condensation zone is not significantly detrimental to the thermal stripping step. If desired, the inner wall may, of course, be insulated.

Figure 3:
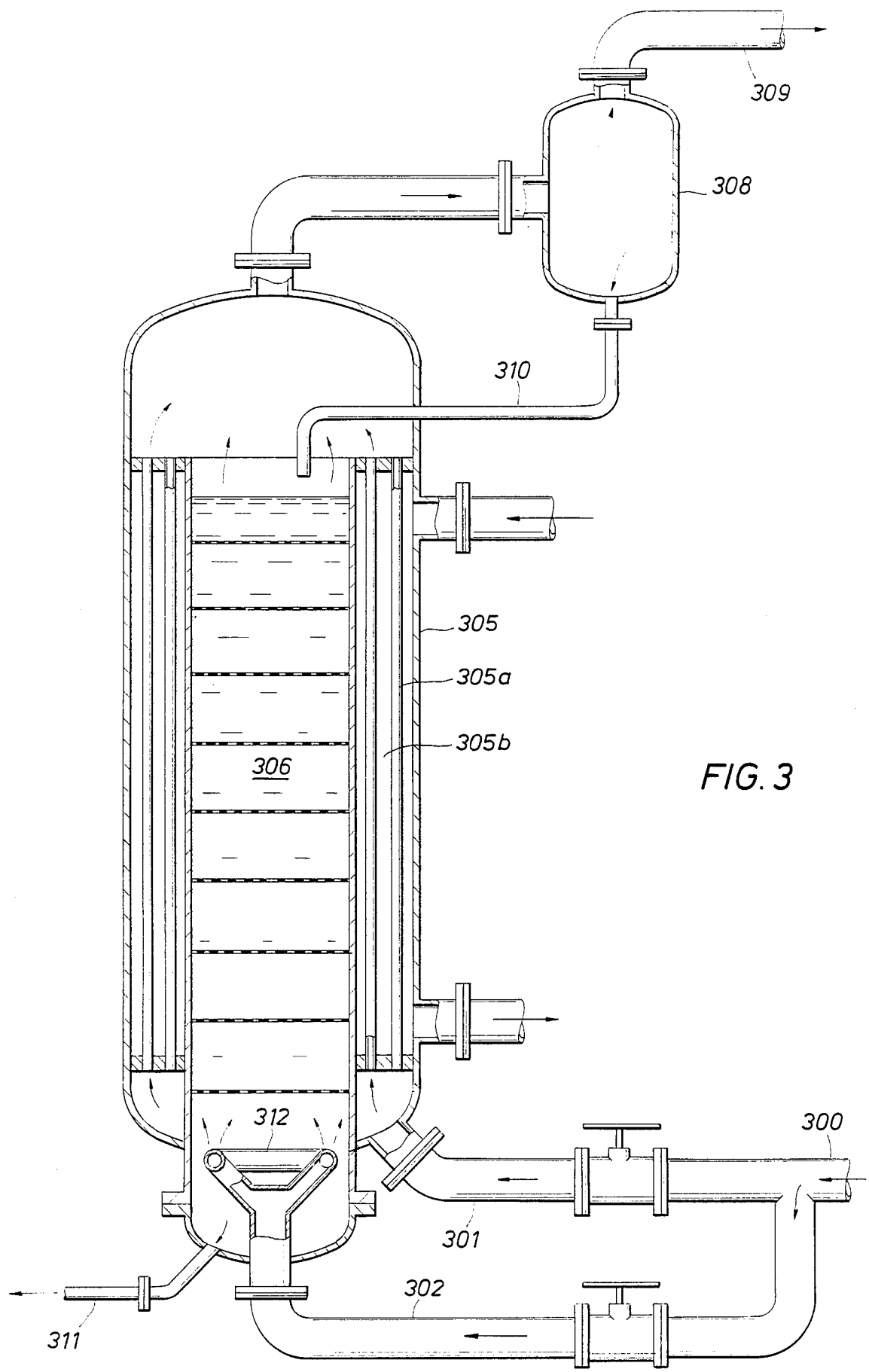
FIG. 3 illustrates another embodiment of the invention also employing an annular tubular exchanger in the first partial condensation zone, however, a central column having perforated baffle plates and operated in a flooded condition is employed in the second partial condensation zone.

In FIG. 3, the embodiment illustrated is basically the same as that illustrated in FIG. 2 except that the second partial condensation zone employs direct heat exchange in a flooded condition. Here, the second portion of the starting gas mixture is introduced at the lower region of the flooded second partial condensation zone through gas sparging means 312 and bubbles upwardly through perforated plates which are completely immersed in the down-flowing, recovered condensates. In this embodiment, thermal stripping of the recovered condensate is augmented by stripping action of the rising gases.

FIG. 4 is a preferred embodiment of the invention that will be described in the overall context of a liquefied natural gas plant where LPG is also produced from $C_3$ to $C_4$ components of the original field gas. In the exemplary facility, normally liquid hydrocarbons comprising $C_5+$ components have been removed by upstream gas/liquid separation so that the starting hydrocarbon gas mixture contains principally $C_1$ to $C_3$ hydrocarbons with smaller amounts of $C_4+$ components. In this illustrative embodiment, it is desired to remove a maximum amount of the $C_3$ component from the starting gas mixture.

The starting gas mixture at a temperature of $-37°$ C. and pressure of 42 kg/cm$^2$ is introduced to the parallel first (405) and second (406) partial condensation zones of the system through line 400 which discharges into the bottom head of the unit in fluid communication with the warm tube sides of each condensation zone. Division of the starting gas into first and second portions is fixed by equalization of pressure drops across the tube sides in each of the partial condensation zones such that the first portion is about 70 mole percent of the starting gas mixture.

A first refrigerant, later described, is introduced through line 407 at a temperature of $-62°$ C. to the cold shell side 405$b$ of the first partial condensation zone and is warmed to $-40°$ C. by giving up refrigeration to the first portion of the starting gas mixture prior to withdrawal through line 413.

The first and second portions of the starting gas flow upwardly through respective tube sides, 406$a$ and 405$b$ of the first and second partial condensation zones at a mass velocity of 140 kg/sec/m$^2$ which entrains $C_3$ and $C_4$ condensate in the remaining first and second light gases so that two phase mixtures flow out of the tubes and are combined in the plenum space 414 above the tubes. The combined two phase mixtures at a temperature of $-51°$ C. are then passed through the first gas/liquid separation zone embodied by vane type impingement separator 408 which separates first and second condensates for introduction through line 410 to the cold shell side 406$b$ of the second partial condensation zone. As indicated in the drawing, cold shell side 406$b$ is operated under flooded condition so that the recovered first and second condensates as well as the later described third condensate are thermally stripped of light gases by the warmer second portion of the starting gas within the tubes. The resulting stripped hydrocarbon condensate containing substantially all of $C_3$ and $C_4$ components of the starting gas mixture is recovered from the second partial condensation zone at a temperature of $-40°$ C.

A second hydrocarbon gas mixture which is lighter than the starting gas mixture and comprising the first and second light gases is recovered from the downstream side of vane separator 408 and introduced to the third partial condensation zone 415 embodied by a second series stage of the system located above the lower stage which embodies the parallel flow first and second partial condensation zones.

The third partial condensation zone is cooled by introduction of a second refrigerant which is a mixed refrigerant containing $C_1$ to $C_5$ hydrocarbons through line 416 at a temperature of $-84°$ C.

The second hydrocarbon mixture passes through the third partial condensation zone in indirect heat exchange with the second refrigerant to form a third condensate entrained in a third light gas. Gas mass velocity in the warm tube side 415$b$ is, again, 140 kg/sec/m$^2$ and a two phase mixture is recovered now from the tube side of the third partial condensation and introduced to a second gas/liquid separation zone embodied by vane separator 417. The third condensate, principally $C_1$ and $C_2$ hydrocarbons, is recovered from this separator and introduced via line 418 to the second partial condensation zone where it is combined with the first and second condensates and supplements refrigeration. In the drawing, the third condensate flows across the upper tubesheet of the annular heat exchanger and drains into the central well of the second partial condensation zone.

Finally, a third hydrocarbon gas mixture lighter than the second hydrocarbon gas mixture and comprising the third light gas is recovered from the downstream side of separator 417 at a temperature of $-62°$ C. and introduced through line 407 to the first partial condensation zone as the first refrigerant. The warmed first refrigerant withdrawn through line 413 contains principally methane along with any nitrogen in the starting gas and a lesser amount of $C_2$ and $C_3$ components that escaped condensation in the first, second, and third partial condensation zones. To the extent that more complete separation of these components may be desired, it is apparent that fourth and subsequent condensation stages in series with the third partial condensation may be employed in which each series stage operates at a lower temperature than the preceding stage.

We claim:

1. A method for partial condensation of a hydrocarbon gas mixture which comprises:
   (a) dividing a starting hydrocarbon gas mixture into at least first and second portions;
   (b) introducing a first refrigerant to a first partial condensation zone;
   (c) passing the first portion through the first partial condensation zone in indirect heat exchange with the first refrigerant to form a first condensate entrained in a first light gas;
   (d) recovering a two phase mixture containing the first condensate and the first light gas from the first partial condensation zone and introducing the recovered two phase mixture to a first gas/liquid separation zone;

(e) recovering the first condensate from the first gas/liquid separation zone;

(f) introducing the recovered first condensate to a second partial condensation zone;

(g) passing the second portion through the second partial condensation zone in heat exchange with the recovered first condensate to form a second light gas and a second condensate and thermally stripping the recovered first condensate and the second condensate;

(h) recovering the second light gas from the second partial condensation zone;

(i) recovering stripped hydrocarbon condensate from the second partial condensation zone at substantially the same pressure as the divided hydrocarbon gas mixture; and (j) recovering a second hydrocarbon gas mixture from the first gas/liquid separation zone.

2. The method of claim 1 wherein the second portion of the starting hydrocarbon gas mixture is passed through the second partial condensation zone in direct heat exchange with the recovered first condensate.

3. The method of claim 1 wherein the second portion of the starting hydrocarbon gas mixture is passed through the second partial condensation zone in indirect heat exchange with the recovered first condensate.

4. The method of claim 1 wherein the velocity of the first light gas passing through the first partial condensation zone is between 25 and 500 kg/sec/m$^2$.

5. The method of claim 1 wherein the first portion of the starting hydrocarbon gas mixture is between 70 and 95 mole percent of the starting hydrocarbon gas mixture.

6. The method of claim 1 wherein the stripped hydrocarbon condensate is recovered from the second partial condensation zone under a hydrostatic head with respect to the divided starting hydrocarbon gas mixture between 3 and 14 meters.

7. The method of claim 1 wherein the starting hydrocarbon gas mixture contains components within the range of $C_1$ to $C_6$ hydrocarbons and the first gas/liquid separation zone is operated at a pressure between 32 and 60 kg/cm$^2$a.

8. The method of claim 1 which additionally comprises introducing the recovered second light gas to the first gas/liquid separation zone.

9. The method of claim 8 which additionally comprises:
(a) introducing a second refrigerant to a third partial condensation zone;
(b) passing the second hydrocarbon mixture through the third partial condensation zone in indirect heat exchange with the second refrigerant to form a third condensate entrained in a third light gas;
(c) recovering a two phase mixture containing the third condensate and the third light gas from the third partial condensation zone and introducing the recovered two phase mixture to a second gas/liquid separation zone;
(d) recovering the third condensate from the second gas/liquid separation zone; and
(e) recovering a third hydrocarbon gas mixture from the second gas/liquid separator.

10. The method of claim 9 which additionally comprises introducing the recovered third condensate to the second partial condensation zone in admixture with the recovered first condensate.

11. The method of claim 9 wherein the first refrigerant introduced to the first partial condensation zone comprises the third hydrocarbon gas mixture.

12. The method of claim 11 wherein the starting hydrocarbon mixture contains principally $C_1$ to $C_3$ hydrocarbons and the second refrigerant introduced to the third partial condensation zone is at a temperature between $-45°$ C. and $-85°$ C.

* * * * *